/

US006472062B1

(12) United States Patent
Neerinck et al.

(10) Patent No.: US 6,472,062 B1
(45) Date of Patent: Oct. 29, 2002

(54) METHOD FOR MAKING A NON-STICKING DIAMOND-LIKE NANOCOMPOSITE

(75) Inventors: Dominique Neerinck, Hertsberge; Peter Persoone, Deinze; Marc Sercu, Roeselare, all of (BE)

(73) Assignee: N.V. Bekaert S.A., Zwevegem (BE)

( * ) Notice: Subject to any disclaimer, the term of this patent is extended or adjusted under 35 U.S.C. 154(b) by 0 days.

(21) Appl. No.: 09/446,308

(22) PCT Filed: Jun. 15, 1999

(86) PCT No.: PCT/EP98/03726

§ 371 (c)(1),
(2), (4) Date: Dec. 20, 1999

(87) PCT Pub. No.: WO98/59089

PCT Pub. Date: Dec. 30, 1998

(30) Foreign Application Priority Data

Jun. 19, 1997 (EP) .............................. 97201867

(51) Int. Cl.[7] .............................. B32B 5/16; B32B 9/04; C23C 16/26; C23C 14/02; H05H 1/00
(52) U.S. Cl. ..................... 428/336; 428/446; 427/249.7; 427/249.11; 427/534; 427/535; 427/577
(58) Field of Search .............................. 428/220, 411.1, 428/332, 334, 446, 447, 923, 926, 932, 336; 520/10, 12, 30–37; 427/534, 535, 577, 249.7, 249.11

(56) References Cited

U.S. PATENT DOCUMENTS

| | | | | |
|---|---|---|---|---|
| 5,112,025 A | * | 5/1992 | Nakayama et al. | 249/115 |
| 5,352,493 A | * | 10/1994 | Dorfman et al. | 427/530 |
| 5,579,583 A | * | 12/1996 | Mehregany et al. | 30/342 |
| 5,618,619 A | * | 4/1997 | Petrmichl et al. | 428/334 |
| 5,638,251 A | * | 6/1997 | Goel et al. | 361/313 |

FOREIGN PATENT DOCUMENTS

| | | |
|---|---|---|
| EP | 0 856 592 | 8/1998 |
| WO | 95/24275 | 9/1995 |
| WO | 97/12757 | 4/1997 |
| WO | 97/40207 | 10/1997 |

OTHER PUBLICATIONS

Dorfman, Benjamin et al., *New Diamond and Diamond–Like Films*, vol. 6, "Diamond–Like Nanocomposite Coatings: Novel Thin Films", pp. 219–226, (1995).

Dorfman, V.F., *Thin Solid Films*, 212, "Diamond–like nanocomposites (DLN)", pp. 267–273, (May 15, 1992).

* cited by examiner

*Primary Examiner*—Paul Thibodeau
*Assistant Examiner*—Sheeba Ahmed
(74) *Attorney, Agent, or Firm*—Foley & Lardner

(57) ABSTRACT

An improved non-sticking diamond-like nanocomposition includes networks of a-C:H and a-Si:O, wherein the H-concentration is between 85% and 125% of the C-concentration. The composition includes preferably 25 to 35 at % of C, 30 to 40 at % of H, 25 to 30 at % of Si, and 10 to 15 at % of O.

21 Claims, No Drawings

METHOD FOR MAKING A NON-STICKING DIAMOND-LIKE NANOCOMPOSITE

FIELD AND BACKGROUND OF THE INVENTION

The invention relates to an improved non-sticking diamond like nanocomposite composition. The substrate surfaces thereby obtain non-sticking properties, and become at the same time very hard, corrosion and wear resistant and self-lubricating. The invention also relates to certain uses of such coated substrates e.g. as moulding means.

Diamond Like Nanocomposite (DLN) compositions consist of an amorphous random carbon network which is chemically stabilized by hydrogen atoms. The carbon network is interpenetrated with an amorphous glass-like silicon network which is chemically stabilized by oxygen atoms (a-C:H/a-Si:O).

In U.S. Pat. No. 5352493 a process is described for coating a substrate with a DLN composition in a vacuum chamber. Thereby a plasma is formed from an organic precursor containing the elements C, H, Si and O to be deposited in a certain proportion. This composition is deposited from the plasma onto the substrate to which a negative DC-bias or RF self-bias voltage is applied.

Most of the conventionally applied deposition processes use high RF-voltage frequencies (up to 25 MHz, typically 13,56 MHz). This renders the upscaling of the process quite difficult.

Moreover, in some known processes very low pressures (less than $3.1^{-4}$ mbar) are applied, making it difficult to apply a homogeneous coating, in particular on a substrate with a complex shape. It is however of great interest with regard to the industrial application of the homogeneous coatings—also on complex parts—to eliminate the need for very complex rotating substrate holders.

An improved DLN coating, deposition process and reactor design are described in applicant's copending patent applications Nos. WO/97/40207 and EP 856 592.

OBJECTS AND DESCRIPTION OF THE INVENTION

It is an aim of the invention to provide a non-sticking homogeneous DLN composition and a flexible process for uniformly coating any substrate with such composition. With a non-sticking coating composition is meant here a DLN offering a surface energy of between 22 and 30 mN/m. It is also an object to provide such a coating with a hardness above 10 GPa.

According to the findings of the inventors, such a non sticking DLN coating needs a relatively high concentration of hydrogen. In particular the H-concentration should be between 85% and 125% of the C-concentration. The composition preferably comprises from 25 to 35 at % C, 30 to 40 at % of H, 25 to 30 at % of Si and 10 to 15 at % of O.

The coating method comprises the steps of
a) plasma etching of the substrate by bombardment of the substrate by ions of an inert gas such as Ar (Reactive Ion Etching, RIE),
b) introducing in the vacuum chamber, which operates at a working pressure of between $5.10^{-3}$ and $5.10^{-2}$ mbar, a liquid organic precursor containing the elements C, H, Si, O to be deposited in suitable proportions, which proportions remain substantially constant during the deposition process,
c) forming a plasma from the introduced precursor by an electron assisted DC-discharge using a filament with a filament current of 50–150 A, a negative filament bias DC voltage of 50–300 V and with a plasma current between 0.1 and 20 A,
d) depositing the composition on the substrate, to which a negative DC-bias or negative RF self-bias voltage of 350 to 700 V is applied, in order to attract ions formed in the plasma; the frequency of the RF voltage being preferably comprised between 30 and 1000 kHz.

The plasma etching step a) of the proposed coating method activates the surface and removes residual oxides from it. This process step is essential for obtaining a good adherence of the coating onto the substrate.

The liquid organic precursor is preferably a siloxane compound such as hexamethyldisiloxane (HMDS), with a relatively high content of Si and O. A polyphenylmethylsiloxane, with a lower content of Si and O, can however also be used as precursor.

Although the use of a filament, e.g. a thoriated W filament, is not necessary for forming the plasma, an electron assisted DC discharge leads to a higher plasma density and thus to a deposition rate which is at least 20% higher than that without use of the filament. The bias voltage influences the properties of the deposited coatings, especially the hardness and the surface energy. The lower the bias voltage, the lower the hardness of the coating (e.g. 12 GPa at 500 V bias voltage, compared to 8 GPa at 300 V bias voltage), and the lower the surface energy. The non-sticking properties of the deposited coatings are indeed better when the coating is deposited at lower bias voltages.

The low RF frequency used in step d) of the proposed coating method facilitates its upscaling.

In a vacuum reactor as described in applicant's copending application WO 97/40207 the precursor is introduced with Ar as a carrier gas. The mixture gas/precursor is delivered in a controllable manner to the vacuum chamber through a controlled evaporation mixing system. The liquid precursor is passed through a liquid mass flow controller to a mixing valve where it is combined with the carrier gas stream. From there it is transferred to a mixing chamber which is heated to about 80° C. to 200° C. The precursor evaporates in the mixture and the hot mixture enters the vacuum chamber.

The working pressure in the vacuum chamber is typically about $5.10^{-3}$ to $5.10^{-2}$ mbar, which is much higher than the pressures being applied in some known processes, favouring a more homogeneous deposition on complex substrates. This working pressure range is preferably between $7.10^{-3}$ and $1.2.10^{-2}$ mbar.

The non-sticking properties of the coating can be expressed in terms of its (low) surface energy and the (high) contact angle of a water droplet on it.

The contact angle of a water droplet on a surface coated with the DLN composition according to the proposed method, has been measured to be 90 to 95°. The surface energy of the deposited DLN coatings typically varies between 25 and 30 mN/m. The surface energy has been determined from the contact angles of certain liquids (demineralized water, formaldehyde, ethylene glycol, hexane) on the coated surface, using a Zisman plot.

If a magnetic field between 5 and 150 Gauss is applied during the deposition of the coating, the plasma is intensified. The magnetic field can be applied e.g. by means of an inductive coil, situated near the thoriated filament in the reactor.

During the deposition process according to the invention, an inert gas can be introduced in the vacuum chamber, ionised and incorporated by ion bombardment of the growing layer. This may lead to a higher nanohardness of the deposited film. The inert gas can be introduced separately or as carrier gas for the precursor.

If desired, one or more transition metals can be codeposited by ion sputtering or by thermal evaporation in order to influence the heat and/or electrical conductivity of the coating.

An example of a coating composition deposited according to the proposed method is as follows: 36% Si, 17% O, and 47% C (leaving H out of consideration). Its surface energy measured 27 mN/m.

In order to lower the surface energy of the deposited coating even more, additional oxygen gas can be added to the. plasma during the coating process. By adding an additional flow of oxygen so that an O-content of 25 to 30% is reached (leaving H out of consideration) an even lower surface energy of 24 mN/m was measured.

The non-sticking, homogeneous DLN coating displays a low surface energy, a high nanohardness, good tribological properties (even under humid conditions), and a controlled heat and/or electrical conductivity.

The composition can be doped with at least one transition metal, such as Zr, Ti or W. The plasma etching step can result in the incorporation into the composition of 0.5 to 5% at of an inert gas, such as Ar, Kr or N.

The coating can therefore be considered as a hard equivalent of teflon, having however a wear resistance far in excess of that of teflon. It is indeed a very important disadvantage of teflon that it is not hard enough to withstand strong mechanical forces.

The proposed non-sticking DLN coating has the additional advantage with respect to teflon that it does not contain any fluorine.

The non-sticking properties of the deposited DLN coating, make it very suitable for many applications, i.a. for those as described in the following examples. The thickness of the coating layer on the substrate is chosen between 0.01 $\mu$m and 10 $\mu$m. The invention provides in particular all kinds of moulding means with e.g. male and female parts ; in the form of shaping pens, pins, pointers, nozzles, dies, stamps and stamp pads etc. The moulding surface of these means is then the substrate onto which the non-sticking DLN coating of the invention is deposited.

EXAMPLES

Example 1

Hard Release Coating for Moulds Used in the Injection Moulding Process

By means of the coating method according to the invention, a non-sticking DLN coating has been successfully applied onto the surface of a mould used for the injection moulding of polyoxymethylene (POM). The adherence of the coating to the substrate was very satisfying, as were the demoulding results in general: no material sticked to the mould when releasing it. The release from the DLN coated mould was much faster than from the non-coated moulds, and no material deformation was observed when removing the moulded articles from the mould. The coating is also useful for mould surfaces for shaping other polymer or other pasty materials by methods such as injection moulding, extrusion, pultrusion or press moulding.

Example 2

Release Coating for an Electrode for Welding Nylon by Fusion

In the nylon welding process, two nylon muff-like workpieces are contacted at their ends with each other. A wire is inserted along and within the central cavity of these two pieces. The wire is then heated by induction or by means of electrical resistances (Joule effect), causing the nylon material in the contact area to melt. Afterwards, when starting to cool down, the wire is pulled out of the nylon workpieces. The nylon material solidifies upon cooling, so that the two workpieces are welded together.

The hot nylon material may in no way stick to the heating wire when pulling it out. This can be prevented by coating the wire with a non-sticking DLN film by means of the method according to the invention.

Commonly a teflon coating is used for this purpose. However, teflon cannot withstand the great mechanical (wear) forces acting on the coating when pulling it out of the cavity. As the tribological properties of the DLN coating are better than those of teflon, and as the DLN coating is much harder than the teflon equivalent, it is more suitable than teflon for this application. Indeed the DLN coated electrode is more durable and thus re-usable for a great number of times.

Example 3

Non-Sticking Coating on Electro-Surgical Blades

In one method for surgical cutting of the human skin or tissue use is made of an electro-surgical cutting blade. Thereby a RF voltage is applied to heat up said blade. The human body acts as the earth pole, so that an electrical current passes through the body, and burns skin or tissue open.

The coating method according to the invention can be used for depositing a non-sticking DLN coating onto the surface of the cutting blade, preventing human tissue or blood from sticking to it.

Various cutting tests were performed on liver and mozzarella cheese simulating the human tissue.

For the mozzarella cutting test a Valleytab Force2 ES generator and power control pencil were employed. The cheese was placed on the return electrode (metal plate) and the coated cutting blade was plugged into the pencil tip. A RF power of 25 W/500 kHz was applied.

The cutting results with respect to the DLN coated blades are excellent. The coated blades perform at least as well as the commonly used teflon-coated ones.

Furthermore, the non-sticking DLN compositions show promising use as coatings on means for processing food, plastics and pharmaceuticals, detergents and other liquid or pasty materials.

What is claimed is:

1. An improved non-sticking diamond-like nanocomposition comprising networks of a-C:H and a-Si:O, wherein the H-concentration is between 85% and 125% of the C-concentration, and wherein the nanocomposition has a hardness of at least 10 GPa as measured by nanoindentation.

2. A composition according to claim 1 comprising 25 to 35 at % of C, 30 to 40 at % of H, 25 to 30 at % of Si and 10 to 15 at % of O.

3. A composition according to claim 1 which is doped with at least one transition metal.

4. A composition according to claim 3 wherein said transition metal is Zr, Ti or W.

5. A composition according to claim 1 comprising 0.5 to 5 at % of an inert gas.

6. A substrate, covered at least in part with a layer of the composition according to claim 1, wherein the thickness of the layer is between 0.01 $\mu$ and 10 $\mu$m.

7. A substrate according to claim 6, wherein said substrate is a moulding mean.

8. A substrate according to claim 6, wherein said substrate is a mould for injection moulding of polymer materials.

9. A substrate according to claim 6, wherein said substrate is an electrode for welding plastic by fusion.

10. A substrate according to claim 6, wherein said substrate is an electro-surgical cutting blade.

11. A process for coating in a vacuum chamber a substrate at least in part with a diamond-like nanocomposite composition, comprising the steps of:

a) plasma etching of the substrate by bombardment of the substrate by ions of an inert gas;

b) introducing in the vacuum chamber, at a working pressure of between $5\times10^{-3}$ and $5\times10^{-2}$ mbar, a liquid organic precursor containing the elements C, H, Si, O to be deposited in proportions, which proportions remain substantially constant during a deposition process;

c) forming a plasma from the introduced precursor by an electron assisted DC-discharge using a filament with a filament current of 50–150 A, a negative filament bias DC voltage of 50–300 V and with a plasma current between 0.1 and 20 A; and d) depositing the composition on the substrate, to which a negative DC-bias or negative RF self-bias voltage is applied, in order to attract ions formed in the plasma, wherein the frequency of the RF voltage is between 30 and 1000 kHz, wherein the diamond-like nanocomposite composition comprises networks of a-C:H and a-Si:O, wherein the H-concentration is between 85% and 125% of the C-concentration, and wherein the diamond-like nanocomposite composition has a hardness of at least 10 GPa as measured by nanoindentation.

12. A process according to claim 11, wherein the organic precursor is an organosilicon compound.

13. A process according to claim 12, wherein the organic precursor is hexamethyldisiloxane.

14. A process according to claim 11, wherein during the deposition process an inert gas is introduced in the vacuum chamber, ionised, and incorporated by ion bombardment into a growing composition layer on the substrate.

15. A process according to claim 11, wherein the precursor is mixed with a carrier gas for introduction in the vacuum chamber and the mixture is heated to evaporate the precursor.

16. A process according to claim 15, wherein the carrier gas comprises an inert gas.

17. A process according to claim 11, wherein at least one transition metal is co-deposited on the substrate by one of ion sputtering and thermal evaporation.

18. A process according to claim 11, wherein the substrate is a mould used for injection moulding of polymer materials, which is coated at least in part with the non-sticking diamond-like nanocomposite composition.

19. A process according to claim 11, wherein the substrate is an electrode for welding nylon by fusion, which is coated at least in part with the non-sticking diamond-like nanocomposite composition.

20. A process according to claim 11, wherein the substrate is an electrosurgical cutting blade, which is coated at least in part with the non-sticking diamond-like nanocomposite composition.

21. A process according to claim 11, wherein, in the step of depositing the composition, the negative DC-bias or negative RF self-bias voltage is between approximately 350 and 700 V.

* * * * *